United States Patent [19]

Joulak et al.

[11] Patent Number: 5,391,683
[45] Date of Patent: Feb. 21, 1995

[54] PREPARATION OF AROMATIC POLYISOCYANATES

[75] Inventors: Faouzi Joulak; Denis Revelant; Pascal Vacus, all of Villeurbanne, France

[73] Assignee: Rhone-Poulenc Chimie, Courbevoie Cedex, France

[21] Appl. No.: 137,352

[22] Filed: Oct. 18, 1993

[30] Foreign Application Priority Data

Oct. 16, 1992 [FR] France .................. 92 12436

[51] Int. Cl.⁶ .................................................. C08G 18/70
[52] U.S. Cl. ..................... 528/67; 560/338; 560/347
[58] Field of Search ............... 528/67; 560/338, 347

[56] References Cited

U.S. PATENT DOCUMENTS 2,480,089  8/1949  Slocombe et al. .................. 528/76

FOREIGN PATENT DOCUMENTS 0289840  11/1988  European Pat. Off. .
656726  8/1951  United Kingdom .
1165831  10/1969  United Kingdom .

*Primary Examiner*—Maurice J. Welsh
*Attorney, Agent, or Firm*—Burns, Doane, Swecker & Mathis

[57] ABSTRACT

Aromatic polyisocyanates, e.g., toluene diisocyanate, are prepared by reacting/contacting at least one aromatic compound (A) bearing at least two primary amine substituents, e.g., toluenediamine, xylylenediamine and/or phenylenediamine,, with phosgene, in gaseous phase and in a reactor/reaction zone devoid of active mechanical stirring.

22 Claims, No Drawings

PREPARATION OF AROMATIC POLYISOCYANATES

BACKGROUND OF THE INVENTION

1. Field of the Invention

The present invention relates to the preparation of aromatic compounds bearing at least two isocyanate substituents, and, more especially, to the preparation of toluene diisocyanate and isomers thereof, whether alone or in admixture.

2. Description of the Prior Art

The preparation of aromatic compounds bearing one or more isocyanate substituents by reacting amines with phosgene in the gaseous phase has long been known to this art, albeit such reaction has essentially been limited to the conversion of monofunctional amines.

Thus, the gas phase phosgenation of aliphatic monoamines such as methylamine or ethylamine, or of aromatic monoamines such as aniline, is described in GB-656,726 (Monsanto). However, the reaction of polyfunctional amines with phosgene is not described.

GB-1,165,831 (ICI) describes the gas phase reaction of aromatic or aliphatic mono- or polyfunctional amines with phosgene with a view to preparing the corresponding isocyanates, such reaction being carried out in a cylindrical reactor fitted with a mechanical stirrer. This process presents disadvantages by reason of the use of rotating components of the mechanical stirrer, in particular problems of sealing at the rotating shaft and problems of fouling and therefore of blocking the stirrer as a consequence of the formation of adhesive reaction byproducts.

SUMMARY OF THE INVENTION

Accordingly, a major object of the present invention is the provision of an improved process for the preparation of aromatic polyisocyanates that avoids or conspicuously ameliorates the above disadvantages and drawbacks to date characterizing the state of this art.

Briefly, the present invention features contacting at least one compound (A) containing at least two primary amine functional groups and at least one aromatic nucleus, with phosgene, in the gaseous phase, and wherein said contacting of reactants is carried out in a reactor/reaction zone devoid of any rotating or moving stirrer.

DETAILED DESCRIPTION OF PREFERRED EMBODIMENTS OF THE INVENTION

More particularly according to the present invention, polyisocyanates corresponding to the conversion of the amines indicated above are prepared without requiring the reaction to be carried out in a reactor fitted with a moving mechanical stirrer. Thus, reactors provided with mechanical stirrers, such as described in GB-1,165,831, are not required.

As indicated above, the process according to the invention comprises contacting at least one compound (A) containing at least two primary amine functional groups and at least one aromatic nucleus, with phosgene, in the gaseous phase.

In a preferred embodiment of the invention, at least one compound (A) is reacted containing at least two primary amine functional groups and at least one $C_6$–$C_{14}$, preferably $C_6$–$C_{10}$, aromatic nucleus, unsubstituted or substituted by one or more linear, cyclic or branched, saturated or unsaturated $C_1$–$C_{10}$ hydrocarbon radicals.

Advantageously, such hydrocarbon radical substituents on said aromatic nuclei are $C_1$–$C_{10}$, preferably $C_1$–$C_6$, alkyl, aryl, alkylaryl and arylalkyl radicals.

The compound (A) is preferably a diamine of the formula:

$$H_2N-R-NH_2 \tag{1}$$

in which R is the unsubstituted or substituted aromatic nucleus described above.

In another preferred embodiment of the invention, at least one compound (A) is employed in which the structural unit R is optionally substituted by one or more $C_1$–$C_{10}$, preferably $C_1$–$C_6$, alkyl radicals.

Benzene and naphthalene nuclei, whether unsubstituted or substituted by one or more methyl, ethyl, propyl, butyl, pentyl or hexyl radicals and/or isomers thereof are particularly exemplary structural units R.

The process of the invention is preferably carried out employing at least one compound (A) selected from among toluenediamine, xylylenediamine and phenylenediamine, whether alone or in admixture, and in the presence or absence of the isomers thereof.

Even more preferably, the compound (A) is toluenediamine.

In general, the process according to the invention is carried out using an excess of phosgene which ranges from 0% to 300 mol %, relative to the number of amine functional groups present in the compound (A). An excess of phosgene which ranges from 10% to 300% and, more particularly, from 10% to 200 mol %, relative to the number of amine functional groups of the compound (A), is preferably employed.

It should be noted that larger quantities do not contribute anything to the reaction, especially in terms of yield.

The reactants brought into contact in the reaction according to the invention, namely, at least one compound (A) and phosgene, may be introduced by themselves, or in the presence of a diluent carrier gas. By "diluent carrier gas" is intended any diluent gas which is inert in respect of the reactants, as well as the reaction products. Other than the inert gases, such as, particularly, nitrogen, it is also possible to employ the vapor of a solvent used to dilute the compound (A) and/or the phosgene. Particularly exemplary such solvents include benzene, xylene, orthodichlorobenzene and monochlorobenzene.

In the event that the compound (A) is dissolved in a solvent, this is present, prior to contact with the phosgene, in a concentration by weight ranging from 3% to 30% in said solvent. This concentration preferably ranges from 10% to 20%.

As indicated above, the reaction according to the invention is carried out in a reactor/reaction zone devoid of any moving stirrer. By "moving stirrer" is intended any conventionally moving mechanical means for stirring, agitating, etc.

The reaction according to the invention may be carried out in any type of reactor, the material of which is compatible with the operating conditions of the subject process. Thus, the reaction may be carried out, especially, in a glass or steel reactor, whether or not alloyed or enamelled.

With respect to the shape of the reactor/reaction zone, it is preferably tubular, albeit other shapes can also be employed.

The introduction of the reactants may variously be carried out. They are preferably introduced via injection by means of a nozzle. Such nozzle may, for example, comprise two concentric tubes, one inserted into the other, defining a central part and an annular part. The compound (A) and phosgene, optionally diluted in a carrier gas, may thus be introduced via the central part or the annular part, the difference being of no consequence.

In another preferred embodiment of the invention, the reactants are introduced under conditions such that there is a turbulent regime in the region of contact of said reactants. Nonetheless, introduction of the reactants in a laminar regime is also envisaged.

More particularly, the Reynolds number of the reactant mixture in the region of contact is at least 3,000, preferably at least 5,000 and more preferably at least 8,000.

For example, such a value of the Reynolds number can be reflected, especially, by a velocity of the gaseous mixture of reactants introduced of from 3 to 15 m/s in the case of a tube diameter of from 2 to 6 mm. These low gas velocities present the advantage of limiting erosion of the material of the reactor.

Other than the velocity of the gaseous mixture of the reactants, this turbulent regime can similarly be obtained via a particular reactor geometry such as, for example, a constriction of the reactor walls or else with any arrangement of static internal obstacles such as, for example, chicanes. The velocity of the gaseous reactant mixture and the reactor geometry can also be combined, optionally including internal obstacles, or any other such means known to this art.

Simply and advantageously, it is not required to maintain the mixture in a turbulent regime once the reactants have been brought into contact. Thus, a flow approximating the piston type is particularly suitable, the degree of conversion increasing along the reactor axis. In this fashion, the velocity of the mixture downstream of the region of contact and as far as the reactor outlet, may vary from 15 m/s to a velocity as low as 0.5 m/s in the event of the diameters indicated above.

The residence time of the reactants in the reactor preferably ranges from 1 to 15 seconds. In a preferred embodiment of the invention, the residence time of the reactants in the reactor ranges from 3 to 6 seconds.

Thus, it has now surprisingly been found that reaction times on this order of magnitude do not decrease the yields of the phosgenation reaction, despite the heat-sensitive nature of the reactants and of the final products.

The temperature at which the phosgenation reaction according to the invention is carried out advantageously ranges from 250° to 500° C. More preferably, said reaction temperature ranges from 300° to 400° C. By "reaction temperature" is intended the temperature prevailing in the reactor.

In yet another preferred embodiment of the invention, the reactants are preheated before contacting each other in the reactor. The temperature for preheating the reactants is typically of the same order of magnitude as that required to carry out the phosgenation.

In the event that the compound (A) is employed in the presence of a solvent, the dissolution of said reactant in its solvent is generally performed beforehand, in liquid phase. The resulting mixture is then vaporized at the temperature required for the reaction, by any means known to this art.

The process according to the invention may be carried out under pressure, at reduced pressure, or at atmospheric pressure, with no adverse consequences. For example, the pressure prevailing in the reactor may range from 0.5 to 1.5 bar absolute. The operation is preferably carried out at a pressure close to atmospheric pressure.

Once the phosgenation reaction has been carried out, the products obtained and the unreacted reactants are separated by any technique well known to this art.

It is possible, for example, to isolate the isocyanate produced by selective condensation of the latter in a suitable solvent.

Where convenience is desired, the solvent is preferably selected such that its boiling temperature is higher than that of the decomposition of the carbamyl chloride corresponding to the isocyanate formed. Selecting a solvent satisfying this criterion avoids a subsequent stage of decomposition of said carbamyl chloride.

Furthermore, this same solvent should preferably condense at a temperature at which the products, such as especially the remaining phosgene and the hydrochloric acid formed, remain in the gaseous state.

The isocyanate recovered is then purified, notably by distillation.

Insofar as the products such as phosgene or hydrochloric acid are concerned, these may be destroyed or consumed by treatment with a base such as sodium hydroxide. They can also be separated by any means per se known to this art, to permit the recycling or reuse thereof.

For example, phosgene can be separated from hydrochloric acid by distillation, or by absorption in a solvent at low temperature, and then recycled into the phosgenation process.

In order to further illustrate the present invention and the advantages thereof, the following specific examples are given, it being understood that same are intended only as illustrative and in nowise limitative.

EXAMPLE 1

The following reagents were introduced into a 250-cm$^3$ stainless steel tubular reactor (length: 60 cm and diameter: 2.3 cm) heated electrically to 320° C.:

(i) via the central part of the injector, 2,4-toluenediamine preheated to 320° C. and diluted in o-dichlorobenzene, at flow rates of 102.5 g/h and 922.5 g/h, respectively;

(ii) via the annular part of the injector, gaseous phosgene preheated to 320° C. at a flow rate of 515.6 g/h, (namely, an excess of approximately 200 mol % relative to the number of amine functional groups).

The Reynolds number of the gaseous mixture after injection was 9,000 in the region of contact (corresponding to a gas velocity of 12 m/s) and 2,600 at the reactor outlet (corresponding to a gas velocity of 0.5 m/s).

The residence time in the reactor was 1.8 seconds.

The pressure in the reactor was 1.3 bar.a. and the temperature 320° C.

The gas mixture exiting the reactor was introduced into a column filled with o-dichlorobenzene at 180° C. at reflux. The toluene diisocyanate (bp=250° C. at 1 bar.a.) was condensed and recovered at the base of the column.

The noncondensables (hydrochloric acid, phosgene) were conveyed to a sodium hydroxide scrubber column.

The yield of toluene diisocyanate based on the toluenediamine introduced into the reactor was 92% with a degree of conversion of 100%.

The residues content [residues/(residues+toluene diisocyanate)], measured by microdistillation, was 7.5%.

EXAMPLE 2

The following reagents were introduced into a reactor identical with that of Example 1 and heated to 320° C.:

(i) via the central part of the injector, 90 g/h of m-phenylenediamine and 810 g/h of o-dichlorobenzene, both vaporized at 320° C.;

(ii) via the annular part of the injector, 515.6 g/h of gaseous phosgene preheated to 320° C. (namely, an excess of approximately 200 mol % relative to the number of amine functional groups).

The residence time in the reactor was 2 seconds.

The other operating conditions were otherwise identical with those of Example 1.

The yield of m-phenylene diisocyanate was 93% based on the m-phenylenediamine introduced, with a residue content of 5.8%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an aromatic polyisocyanate, comprising reacting in gaseous phase at least one aromatic compound (A) bearing at least two primary amine substituents, with phosgene, and in a reaction zone devoid of mechanical stirring.

2. The process as defined by claim 1, said at least one aromatic compound (A) comprising at least one $C_6$–$C_{14}$ aromatic nucleus, unsubstituted or substituted by one or more linear, cyclic or branched, saturated or unsaturated, $C_1$–$C_{10}$ hydrocarbon radicals.

3. The process as defined by claim 2, said at least one aromatic nucleus of said at least one aromatic compound (A) being unsubstituted or substituted by one or more $C_1$–$C_{10}$ alkyl, aryl, alkylaryl or arylalkyl radicals.

4. The process as defined by claim 2, said at least one aromatic compound (A) having the formula:

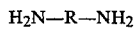  (1)

in which R is an aromatic nucleus.

5. The process as defined by claim 4, wherein said at least one aromatic compound (A) of formula (1), R is a $C_6$–$C_{10}$ aromatic nucleus, unsubstituted or substituted by one or more $C_1$–$C_6$ alkyl radicals.

6. The process as defined by claim 5, said at least one aromatic compound (A) comprising toluenediamine, xylylenediamine, phenylenediamine, or admixtures thereof, in the presence or absence of their isomers.

7. The process as defined by claim 1, comprising reacting an excess of phosgene ranging from 0% to 300 mol %, based on the number of amine functional groups present in said aromatic compound (A).

8. The process as defined by claim 7, comprising reacting an excess of phosgene ranging from 10% to 300%, based on the number of moles of amine functional groups present in said aromatic compound (A).

9. The process as defined by claim 1, said at least one aromatic compound (A) and/or said phosgene being entrained in a diluent carrier gas.

10. The process as defined by claim 1, said at least one aromatic compound (A) being dissolved in solvent vapors therefor, in a concentration by weight ranging from 3% to 30%.

11. The process as defined by claim 1, carried out in a tubular reaction zone.

12. The process as defined by claim 1, comprising reacting in a zone of turbulent regime.

13. The process as defined by claim 1, the Reynolds number of the mixture of reactants in said reaction zone being at least 3,000.

14. The process as defined by claim 13, said Reynolds number being at least 5,000.

15. The process as defined by claim 14, said Reynolds number being at least 8,000.

16. The process as defined by claim 11, the velocity of the gaseous mixture of reactants ranging from 3 to 15 m/s for a tubular reaction zone having a diameter of from 2 to 6 mm.

17. The process as defined by claim 1, comprising reacting in a zone of laminar regime.

18. The process as defined by claim 1, the mixture of gases exhibiting essentially piston flow downstream of said reacting.

19. The process as defined by claim 1, carried out at a residence time of from 1 to 15 seconds.

20. The process as defined by claim 19, carried out at a temperature ranging from 250° to 500° C.

21. The process as defined by claim 20, carried out at about atmospheric pressure.

22. The process as defined by claim 1, further comprising isolating said aromatic polyisocyanate via selective condensation thereof in a solvent having a boiling point higher than the temperature of decomposition of the carbamyl chloride corresponding to said at least one aromatic compound (A).

* * * * *